United States Patent [19]
Pagan

[11] Patent Number: 5,655,528
[45] Date of Patent: Aug. 12, 1997

[54] INTRODUCERS

[75] Inventor: Eric Pagan, Kent, England

[73] Assignee: Smiths Industries Public Limited Company, London, England

[21] Appl. No.: 604,747

[22] Filed: Feb. 23, 1996

[30] Foreign Application Priority Data

Mar. 17, 1995 [GB] United Kingdom ............... 9505399

[51] Int. Cl.[6] .................... A61M 16/00; A62B 9/06
[52] U.S. Cl. ............... 128/207.14; 128/207.15; 128/200.26
[58] Field of Search .................. 606/108, 196; 128/207.14, 207.15, 200.26, 859, 860; 623/9

[56] References Cited

U.S. PATENT DOCUMENTS 4,198,970  4/1980  Luomanen .
5,024,218  6/1991  Ovassapian et al. ............. 128/207.14

*Primary Examiner*—Robert A. Hafer
*Assistant Examiner*—Justine R. Yu
*Attorney, Agent, or Firm*—Pollock, Vande Sande & Priddy

[57] ABSTRACT

An introducer along which a laryngeal mask airway can be slid into position has an open, curved channel portion shaped to extend, in use, from a mouth of a patient to the region of the patient's pharynx. At its machine end, the introducer is bifurcated into two arms extending along opposite sides of the airway, the thickness of the arms being sufficient to protect the airway from damage by the patient's teeth. The arms are curved in an opposite sense from the curvature of the channel portion so that they extend over the upper lip of the patient. A curved bridge piece extends between the two arms and lies against the skin between the patient's nose and mouth.

12 Claims, 2 Drawing Sheets

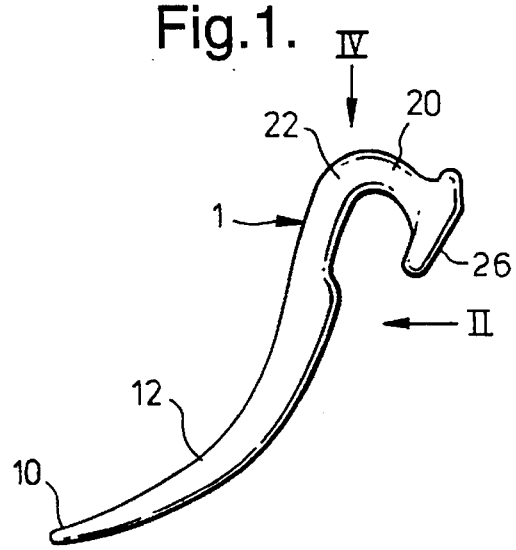
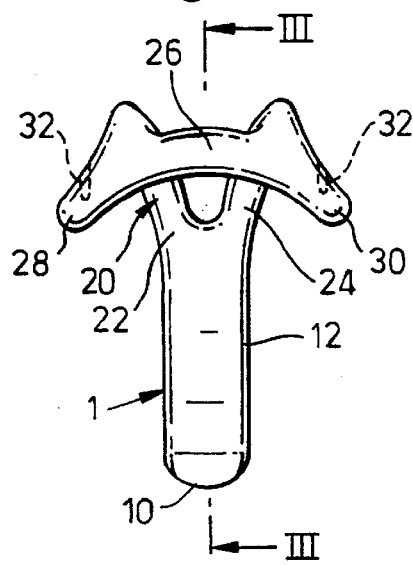
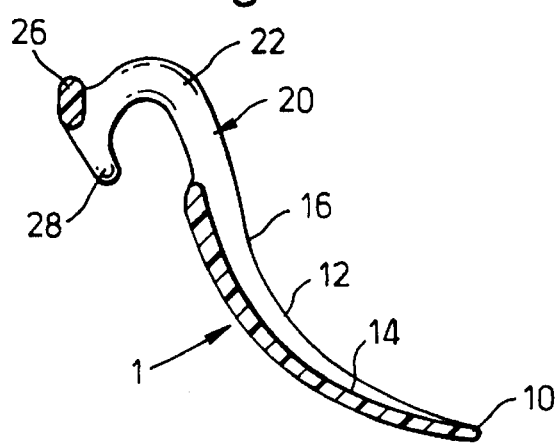
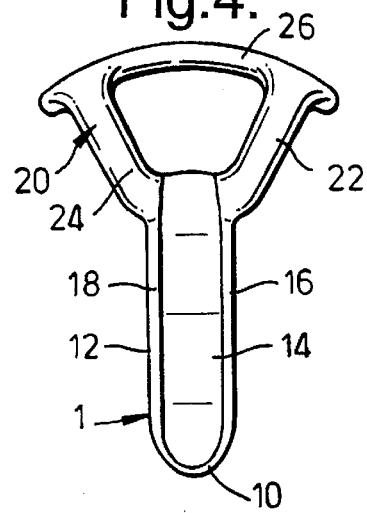
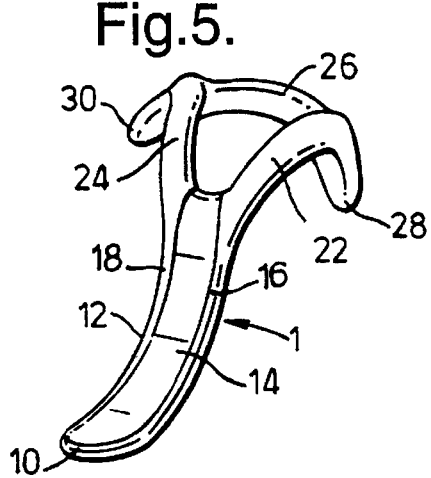
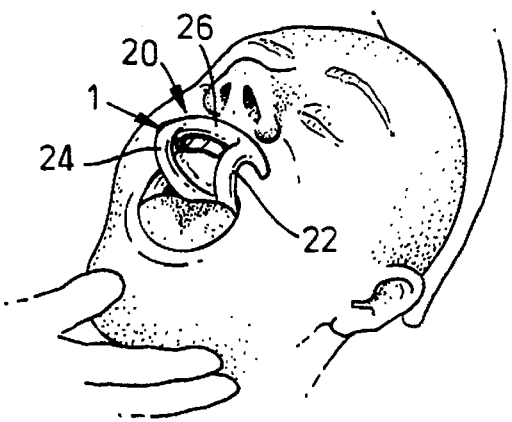

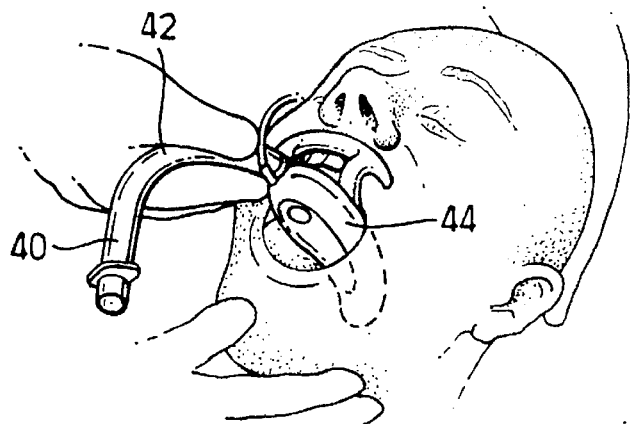
Fig.7.
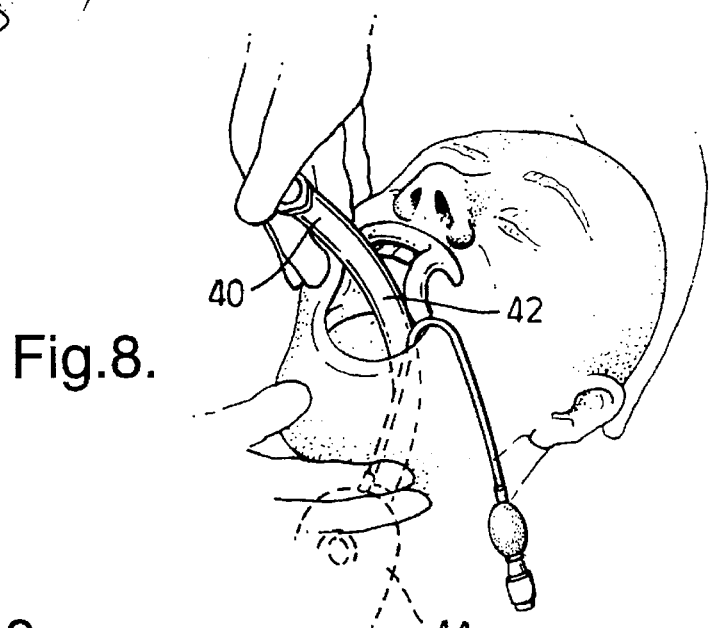
Fig.8.
Fig.9.
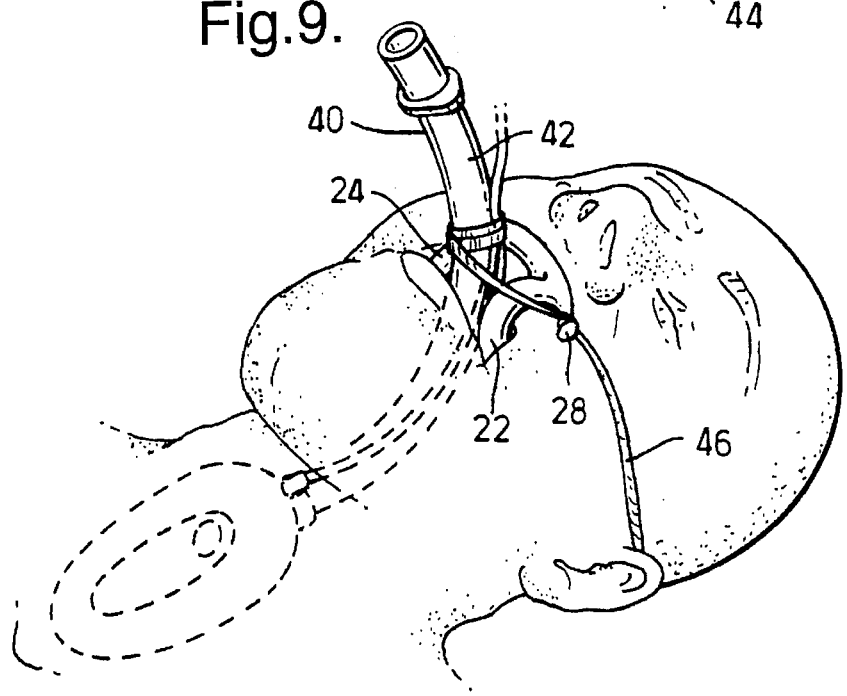

INTRODUCERS

BACKGROUND OF THE INVENTION

This invention relates to introducers for facilitating insertion of a tubular airway to the pharynx or trachea and to assemblies comprising an introducer and airway.

It is common practice to use an airway known as a laryngeal mask for the administration of anesthetic and ventilation gases to a patient. These airways comprise a tube with a mask or cuff at one end, the tube being inserted via the patient's mouth so that one end is located in the hypopharynx and so that the mask forms a seal in this region with the surrounding tissue. Laryngeal masks have several advantages over other airways, such as endotracheal tubes, which are longer and seal with the trachea below the vocal folds. One problem, however, with laryngeal masks is that insertion can cause trauma to the pharyngeal wall. This is because the tip of the mask has a tendency to stick in the pharynx as a result of the sharp turn it has to negotiate before it seats itself in the hypopharynx. These problems have been reported in, for example, Anesthesia 1989; 44:703 by van Heerden and Kirrage. Although the risk of damage can be reduced by ensuring that the head of the patient is correctly positioned during insertion, where the anesthesiologist is not completely familiar with the correct technique, there is still an associated risk of trauma. Blood is often seen on the laryngeal mask when it is removed, even when the anesthesiologist is experienced in the technique. Problems can also be experienced introducing endotracheal tubes.

In GB 2259454 there is described an introducer for a laryngeal mask, which can be used to facilitate insertion and reduce the risk of injury to the patient. One problem with this introducer is that it affords little protection to the mask in the region of the patient's teeth, so there is the risk that the patient could bite the mask causing it to occlude or be damaged. This means that some separate means must be used to protect the tube.

BRIEF SUMMARY OF THE PRESENT INVENTION

It is an object of the present invention to provide an improved introducer device.

According to one aspect of the present invention there is provided an introducer device for use in introducing a tubular airway into a patient, the introducer including an elongated channel-shape member that is open along its entire length, is curved along a major part of its length and extends from outside the mouth of the patient to at least the region of the pharynx such that, in use, a part of the length of the device lies adjacent the hard palate of the mouth, the device being bifurcated in the region of the patient's teeth into two arms extending along opposite sides of the airway, and a thickness of the arms in the region of the teeth being at least substantially equal to a diameter of the airway in that region so that the airway is protected from damage by the patient's teeth.

The aforementioned two arms are preferably curved in an opposite sense from the channel-shape member so that they extend over the upper lip of the patient. The introducer device preferably includes a bridge piece extending laterally between the two arms close to the machine end of the introducer, and the bridge piece may be curved along its length to lie against the skin of the patient between his nose and mouth. The ends of the arms are preferably shaped so that a tie securing the introducer to the patient's head can be wrapped around the arms to retain the introducer in position.

The introducer device may have at least one slot for receiving a tie so that the introducer can be secured to the patient's head. The introducer device is preferably an integral molding of a plastics material and may include a light guide.

According to another aspect of the present invention there is provided an assembly comprising an introducer device having the preceding configuration, and a tubular airway slidable along the introducer device.

The tubular airway is preferably a laryngeal mask.

An introducer device according to the present invention, will now be described, by way of example, with reference to the accompanying drawings.

BRIEF DESCRIPTION OF THE DRAWINGS

FIG. 1 is a side elevation view of the introducer;

FIG. 2 is a rear elevation view of the introducer along the arrow II in FIG. 1;

FIG. 3 is a cross-sectional side elevation view along the line III—III of FIG. 2;

FIG. 4 is a front elevation view of the introducer along the arrow IV in FIG. 1;

FIG. 5 is a perspective view of the introducer; and

FIGS. 6 to 9 illustrate steps in use of the introducer.

DETAILED DESCRIPTION OF THE PREFERRED EMBODIMENT

With reference to FIGS. 1 to 5, the introducer device 1 is about 100 mm long and is moulded from a soft plastics material, such as PVC, or a natural or synthetic rubber. The introducer device can be moulded as a single, integral moulding or made from separate parts moulded together. Alternatively, different parts of the device could be made separately and subsequently clipped or joined together is some other way. The patient end or forward tip 10 of the introducer is rounded and is about 18 mm wide. A channel-shape portion 12 extends rearwardly from the tip along the major part of the length of the introducer and is curved with a radius of curvature of about 58 mm, the channel being open on the inside of the curve. The channel portion 12 has a flat floor 14 across its width and has two shallow walls 16 and 18 along opposite edges, which project from the concave side and increase in height from the patient end 10 to be about 8 mm high at the rear, or machine, end of the portion. The channel-shape portion 12 is about 80 mm long and joins at its machine end with a bite block region 20.

The bite block region 20 is formed by bifurcating, or dividing the device into two arms 22 and 24 at the machine end of the channel portion 12. The arms 22 and 24 are thickened and are of substantially circular section, being about 8 mm in diameter. The arms 22 and 24 incline away from one another at an angle of about 50° and initially extend in a flat plane that is a continuation of the plane which includes the machine end of the channel portion 12. After about 20 mm, the two arms 22 and 24 curve in the opposite direction from the channel portion 12 through a relatively tight curve with a radius of about 8 mm and continue for a distance of about 15 mm. At their machine end, the arms 22 and 24 are joined by a laterally-extending bridge piece 26, which is about 10 mm wide and about 5 mm thick. The bridge piece 26 is curved along its length with a center of curvature coincident with the intersection of the axes of the two arms 22 and 24, as shown in FIG. 4. The bridge piece 26 is also curved along its length in a plane including the width of the bridge piece so that opposite ends of the bridge piece extend downwardly. The bridge piece is extended at its ends beyond the arms to a width of about 62 mm to form two bollards 28 and 30 with smoothly rounded ends.

The dimensions and shape of the introducer 1 are selected to conform to the anatomy of the patient so that the channel portion 12 extends along the hard palate with the tip 10 being located in the pharynx. In this position, the two arms 22 and 24 project between the teeth of the patient and curve cephaladly over the upper lip, with the bridge piece 26 extending along the skin between the nose and the mouth.

The introducer 1 is used by first placing the patient in the usual position for introduction of an oral tube or laryngeal mask, with his neck flexed, his head rotated back and his mouth open, as shown in FIG. 6. The introducer 1 is lubricated over the channel portion 12 on both sides, such as with a hydrophilic gel, and is gripped by the bite block region 20 with the tip 10 pointing down the patient's mouth and with the open side of the channel 12 directed caudally. The forward end of the introducer 1 is pushed into the patient's mouth so that the convex side of the channel portion 12 slides smoothly over the hard palate and pharynx until the arms 22 and 24 extend between the teeth, with the bridge piece 26 lying against the skin just above the upper lip. In this position the tip 10 of the introducer lies in the region of the pharynx. The introducer 1 is relatively flexible at its patient end, because of the low height of the side walls 16 and 18 at the patient end 10, so that it readily conforms to the patient's anatomy as it is slid into position, without trauma. Damage to the patient's teeth during insertion is also avoided because of the flexible nature of the introducer. When correctly located, the introducer provides a guide along which an airway can be inserted.

As shown in FIGS. 7 to 9, the airway 40 is a laryngeal mask of conventional form, such as described in GB 2111394, and comprises a curved tube 42 opening at one end into a cuff or hollow mask 44 located on one side of the tube. In use, the mask 44 conforms to the space behind the larynx and seals around the circumference of the laryngeal inlet but without penetrating the larynx itself. The airway 40 is inserted in the manner shown in FIG. 7, by directing the open side of the mask 44 away from the introducer and resting it on the two arms 22 and 24, with the tip of the mask contacting the machine end of the channel portion 12 of the introducer just inside the patient's mouth. The gap between the two arms 22 and 24 is not sufficient to receive the mask 44, while the width of the channel portion 12 of the introducer 1 is such that the tubular component 42 of the airway is received snugly within it, with the mask overlapping the edges of the channel on both sides. The airway 40 is then slid along the introducer, in the manner shown in FIG. 8, which guides it to the position shown in FIG. 9. Because the introducer 1 is located between the airway 40 and the patient's tissue, it protects the pharynx and hard palate from the airway, thereby reducing trauma. The flexible nature of the introducer enables it to mould itself to the shape of the palate and pharynx as the mask is inserted, thereby reducing localized pressure on the patient's tissue.

The thickness of the arms 22 and 24 where they project between the teeth is sufficient to act as a bite block on either side of the tubular part 42 of the airway 40. In this respect, the thickness of the arms 22 and 24 is preferably at least equal to the diameter of the tubular part of the airway but it will be appreciated that sufficient protection may be afforded to the airway if the arms are slightly thinner than the airway because, although the teeth may contact the airway they would not be able to compress the airway sufficiently to occlude or damage it. The bridge piece 26 limits the extent of insertion of the introducer 1 and thereby prevents the patient swallowing the device.

After the airway 40 has been introduced, the introducer 1 can be readily removed. The open-sided construction along the entire length of the introducer 1 enables the airway 40 to be inserted and the introducer to be removed from the airway without the mask portion 44 or any connector at the machine end of the airway providing an obstruction to this.

In some applications, it may be preferable to leave the introducer 1 in position while the patient is ventilated through the airway 40, so as to avoid the need to use a different bite block. In these circumstances, a ribbon or tie 46 encircling the head of the patient may be wrapped around the machine end of the airway and around the bollards 28 and 30 so as to stabilize the airway, as shown in FIG. 9. Alternatively, the bollards 28 and 30 could be formed with slots 32, as indicated by the broken lines in FIG. 2, so that the ribbon could be retained simply by jamming it into the slots, without having to be wound around the bollards.

The introducer can be readily modified for use in introducing other airways such as, for example, endotracheal tubes. It will be appreciated that the introducer device could be made in different sizes for patients of different sizes, such as adults and children.

The introducer could be made of a light-transmitting material so that it can be used as a light guide for illumination. Alternatively, the introducer could contain within it a fibre-optic cable or other light guide for illumination and viewing of a surgical procedure at the rear of the device.

What I claim is:

1. An introducer device for use in introducing a tubular airway into a patient, the introducer device comprising: an elongated channel-shape member, said channel shape being open on one side along the entire length of said member, said member being curved along a major pan of its length, said open channel shape being on an inside of the curve, said member in use being adapted to extend from outside the mouth of a patient to at least the region of the patient's pharynx such that a part of the length of the introducer device lies adjacent the hard palate of the patient's mouth; and two arms formed by a bifurcation of the portion of said introducer device to be located in the region of the patient's teeth, said two arms being located to extend along opposite sides of said tubular airway, and the arms having a thickness in the portion to be located in the region of the patient's teeth which is at least substantially equal to a diameter of said tubular airway so that said tubular airway is protected from damage by the patient's teeth.

2. An introducer device according to claim 1, wherein said arms curve in an opposite direction from the curvature of said channel-shape member so as to extend, in use, over the upper lip of the patient.

3. An introducer device according to claim 1 including a bridge piece which extends laterally between said two arms close to a machine end of said introducer device.

4. An introducer device according to claim 3, wherein said bridge piece is elongated and curved along its length to lie, in use, against the skin of the patient between the patient's nose and mouth.

5. An introducer device according to claim 1, wherein the said arms have ends shaped to receive a tie that can be wrapped around the arms to retain the introducer device, in use, in position.

6. An introducer device according to claim 1, wherein said introducer device has at least one slot for receiving a tie that secures said introducer device, in use, to the patient's head.

7. An introducer device according to claim 1, wherein said introducer device is an integral moulding of a plastics material.

8. An introducer device according to claim 1, wherein the introducer device is of a transparent material to form a light guide.

9. An introducer device for use in introducing a tubular airway into a patient, the introducer device comprising: an elongated integral channel-shape member of a plastics material, said channel shape being open on one side thereof along the entire length of said member, said member being curved along a major part of its length, said open channel shape being on an inside of the curve, said member in use being adapted to extend from outside the mouth of the patient to at least the region of the patient's pharynx such that a part of the length of the introducer device lies adjacent the hard palate of the patient's mouth; two arms formed by bifurcation of the portion of said introducer device to be located, in use, in the region of the patient's teeth so as to extend along opposite sides of said airway, said two arms having a curve in a direction opposite from the curve of said channel-shape member so as to extend, in use, over the upper lip of the patient, said arms having a thickness in the region of the patient's teeth which is at least substantially equal to a diameter of said airway so that, in use, said airway is protected from damage by the patient's teeth; and a bridge piece extending laterally between said arms at a machine end of the introducer device, said bridge piece being shaped to lie, in use, against the skin of the patient between the patient's mouth and nose.

10. An assembly comprising: a tubular airway and an introducer device for use in introducing said tubular airway into a patient, wherein the introducer device includes an elongated channel-shape member along which said tubular airway is slidable, said channel shape being open on one side along the entire length of said member, said member being curved along a major part of its length, said open channel shape being on an inside of the curve, said member in use being adapted to extend from outside the mouth of the patient to at least the region of the patient's pharynx such that a part of the length of the device lies adjacent the hard palate of the patient's mouth; and two arms formed by a bifurcation of said device, said two arms being located, in use, in the region of the patient's teeth, said two arms extending along opposite sides of said tubular airway, and a thickness of said arms to be located in the region of the patient's teeth being at least substantially equal to a diameter of said tubular airway so that said tubular airway is protected, in use, from damage by the patient's teeth.

11. An assembly according to claim 10, wherein said tubular airway is a laryngeal airway.

12. An assembly comprising: a laryngeal airway and an introducer device for use in introducing a patient end of the airway into the pharynx of a patient, wherein the introducer device comprises: an elongated integral channel-shape member of a plastics material, said channel shape being open on one side thereof along the entire length of said member, said elongated member being curved along a major part of its length, said open channel shape being on an inside of the curve, said member in use being adapted to extend from outside the mouth of the patient to the region of the patient's pharynx such that a part of the length of the introducer device lies adjacent the hard palate of the patient's mouth; two arms formed by a bifurcation of said introducer device, said arms being located in use in the region of the patient's teeth so as to extend along opposite sides of said laryngeal airway, said two arms being curved in a direction opposite to the curvature of said elongated member to extend in use over the upper lip of the patient, a thickness of said arms to be located in the region of the patient's teeth being at least substantially equal to a diameter of said airway so that said airway is protected from damage by the patient's teeth; and a bridge piece extending laterally between said arms at a machine end of the introducer device, said bridge piece being shaped to lie, in use, against the skin of the patient between the patient's mouth and nose.

\* \* \* \* \*